United States Patent [19]

Haughland et al.

[11] Patent Number: 5,262,545

[45] Date of Patent: Nov. 16, 1993

[54] FLUORESCENT CHLORAMPHENICOL DERIVATIVES FOR DETERMINATION OF CHLORAMPHENICOL ACETYLTRANSFERASE ACTIVITY

[75] Inventors: Richard P. Haughland; Hee C. Kang, both of Eugene, Oreg.; Steven L. Young, Menlo Park, Calif.; Michael H. Melner, Aloha, Oreg.

[73] Assignee: Molecular Probes, Inc., Eugene, Oreg.

[21] Appl. No.: 722,352

[22] Filed: Jun. 18, 1991

Related U.S. Application Data

[63] Continuation of Ser. No. 321,494, Mar. 9, 1989, abandoned.

[51] Int. Cl.$^5$ ............... C07F 5/02; C07D 271/12; C07D 219/06; C07D 311/16
[52] U.S. Cl. ................... 548/405; 435/15; 546/103; 549/288; 549/388; 549/394; 564/86; 564/180; 548/126
[58] Field of Search ............................ 548/405

[56] References Cited

U.S. PATENT DOCUMENTS 4,420,568 12/1983 Wang .................................. 549/223
4,774,339 9/1988 Haugland et al. .................. 548/405

OTHER PUBLICATIONS

Alter et al, *Biotechniques* 6, 526 (1988).
Felber, *Science*, 239, p. 184 (1988).
American Heritage Dictionary, (2nd edition, College) p. 324(1976).
Gerson, Benjamin, MD, "Fluorescence Immunoassay," *Journal of Clinical Immunoassay,* vol. 7, No. 1, pp. 73-81, Spring 1984.
Neumann, J. R., "A Novel Rapid Assay for Chloramphenicol Acetyltransferase Gene Expression," *BioTechniques,* vol. 5, No. 5, pp. 444-447, 1987.
Ellis, et al., "Mechanistic Studies of Chloramphenicol Acetyltransferase," *Biochemical Society Transactions,* vol. 15, pp. 867-868, 1987.
Gorman, et al., "Recombinant Genomes Which Express Chloramphenicol Acetyltransferase in Mammalian Cells," *Molecular and Cellular Biology,* vol. 2, No. 9, pp. 1044-1051, Sep. 1982.
Young, et al., "Laboratory Methods—Detection of Chloramphenicol Acetyl Transferase Activity in Transfected Cells: A Rapid and Sensitive HPLC-based Method," *DNA,* vol. 4, No. 6, pp. 469-475, 1985.
Burzio, et al., "Assay of Chloramphenicol Acetyl Transferase by High-Performance Liquid Chromatography," *Gene Anal. Techn.,* vol. 5, pp. 5-8, 1988.

*Primary Examiner*—Mark L. Berch

[57] ABSTRACT

Fluorescent compounds useful in the determination of chloramphenicol acetyltransferase (CAT) enzyme activity are described. The compounds are fluorescent derivatives related in structure to chloramphenicol comprising a base,

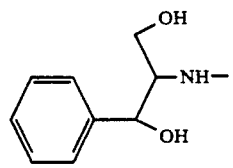

substituted at one to five aromatic ring positions by substituents, which may be the same or different, that are alkyl-, hydroxy-, alkoxy-, aryl-, halo-, nitro-, amino-, alkylamido-, or arylamido-; and a fluorescent moiety linked to the base at —NH— by an aliphatic chain of 1-12 atoms other than hydrogen, where such atoms are carbon, nitrogen, oxygen, or sulfur, or combinations thereof. The substrate compounds are acylated in the presence of CAT to produce fluorescent mono- and diacylated products, which are then physically separated from the reaction mixture and quantitated by means of their fluorescence and/or absorbance. Fluorescent molecules conjugated to chloramphenicol include derivatives of fluorescein, rhodamine, coumarin, dimethylaminonaphthalene sulfonic acid (dansyl), pyrene, anthracene, nitrobenzoxadiazole (NBD), acridine and dipyrrometheneboron difluoride.

8 Claims, 1 Drawing Sheet

FLUORESCENT CHLORAMPHENICOL DERIVATIVES FOR DETERMINATION OF CHLORAMPHENICOL ACETYLTRANSFERASE ACTIVITY

This invention was made with government support under grants nos. 5 P51 RR00163 and GM 38987 awarded by the National Instituted of Health. The government has certain rights in this invention.

This is a continuation of application Ser. No. 07/321,494, filed on Mar. 9, 1989, now abandoned.

FIELD OF THE INVENTION

This invention describes fluorescent compounds useful in the determination of chloramphenicol acetyltransferase (CAT) enzymatic activity. The measurement of CAT activity is widely used to study transcriptional control sequences in a number of fields, some of which include endocrinology, microbiology, virology, genetics, oncology, developmental biology and molecular biology.

BACKGROUND OF THE INVENTION

The study of gene expression has required the development of genes which are relatively easy to assay and can serve as markers to monitor expression of foreign genetic material which has been introduced into cells. The foreign genomic DNA fragments are inserted into a recombinant plasmid along with a marker gene, and after introduction of the plasmid into the target cell, the quantity of protein coded for by the marker gene is determined. When compared to the quantity of protein produced by a plasmid without the insert, the result is indicative of the activity of the inserted fragment.

Marker genes which have been used for this purpose fall into two main categories: those which code for proteins which are detected by antibodies and those which code for proteins which are detected by their enzyme activity. Genes in the first category require the production of specific antibodies to the protein and development of a suitable detection method for measurement of antibody-protein binding. The second group includes genes which code for enzymes such as betagalactosidase, glucuronidase, thymidine kinase, and chloramphenicol acetyltransferase (CAT).

Enzyme marker genes have the advantage of being easy to assay by simply measuring enzyme activity in the cellular extract, while immunoassay-based systems require the development of specific antibodies and an immunoassay technique which may be complex and tedious. However, many enzyme assays are subject to background interference by endogenous enzyme activity in the cells being measured. The CAT gene from bacteria is not normally found in mammalian cells and therefore offers the benefit of a simple, sensitive enzyme-based assay which is free from background interference.

Use of the CAT gene as a marker for measuring promoter function in transfected recombinants was first described by Gorman, et. al, "Recombinant Genomes which Express Chloranphenicol Acetyltransferase in Mamalian Cells," *Mol. Cell Biol.* 2:1044 (1982). In this work, CAT enzyme activity in cell extracts was measured by extracting the [$^{14}$C]chloramphenicol mixture into an organic solvent (ethyl acetate) and separating the mono- and di-acetates by thin-layer chromatography on silica gel. After autoradiography of the separated chloramphenicol derivatives, the spots were cut from the plates and counted to give a quantitative estimate of CAT activity. Other investigators [Young, et. al., "Detection of Acetyltransferase Activity in Transfected Cells: A Rapid and Sensitive HPLC-Based Method," *DNA* 4(6):469 (1985) and Burzio, et. al., "Assay of Chloramphenicol Acyltransferase by High-Performance Liquid Chromatography, *Gene Anal. Techn.* 5:5 (1988)]have measured CAT activity by HPLC of the organic extract and claim sensitivity equivalent to the original TLC method with the added advantage of a substantial reduction in processing time and the elimination of radioactive materials. A third method for assaying CAT was reported by Neumann, et. al., "A Novel Rapid Assay for Chloramphenicol Acetyltransferase Gene Expression," *Biotechniques* 5(5):444 (1987). Using [$^3$H]acetyl Coenzyme A (which transfers acetyl to chloramphenicol in the enzymic process), the cell incubation was performed in a scintillation vial overlaid with scintillation cocktail. Under these conditions, the only radioactive product that diffuses into the cocktail is acetylated chloramphenicol, allowing kinetic analysis through direct measurement of the radioactivity without requiring a manual separation step. This method is fast and convenient, but requires expensive and hazardous radioactive materials of high specific activity.

The use of fluorescence as a means of detection in enzyme assays and immunoassays is recognized to provide many advantages over methods that employ spectrophotometry or measurement of radioactivity for detection [Gerson, "Fluorescence Immunoassay," *J. Clin. Immunoassay* 7(1):73 (1984)]. Among these advantages is the elimination of the danger and expense of handling radioactive materials and the higher potential sensitivity afforded by measurement of a fluorescent signal as compared to spectrophotometry. Higher sensitivity provides, in turn, the potential advantages of greater accuracy and faster assay times.

SUMMARY OF THE INVENTION

In the determination of CAT enzyme activity, the fluorescent chloramphenicol derivative is acylated in the presence of CAT to produce fluorescent mono- and diacylchloramphenicol derivatives which are then separated by thin layer chromatography (TLC), high performance liquid chromatography (HPLC) or other suitable means and quantitated by measurement of their fluorescence and/or absorbance.

Although fluorescent chloramphenicol derivatives have been reported for use in immunoassays [U.S. Pat. No. 4,420,568 (Wang et al. 1983)], as bactericidal dyes [Soviet Union Patent No. 392,716 (Liverant)] and in drug detection [Nowicki, "Studies on Fluorescamine. Part II—Thin-layer Chromatographic Mobilities of Fluorescamine Positive Drugs," *Analytical Letters* 12(A9):1019 (1979)], no fluorescent derivatives of chloramphenicol have been described which have been used as substrates for CAT. In order to be useful for this purpose, a fluorescent chloramphenicol derivative must be soluble in aqueous media near physiological pH, act as an effective substrate for the enzyme and have acylation products with high fluorescence efficiency which can be easily separated from the starting material.

Fluorescent chloramphenicol derivatives which are the subject of this invention exhibit spectral properties which are, for the most part, comparable to fluorescein or 7-dimethylaminocoumarin, both of which have high absorbance and display fluorescence with high quantum efficiency. The subject compounds are soluble in aqueous media at pH 7.0–8.0 at concentrations greater than the $K_m$ (the Michlis-Menton constant or the concentration at half maximum velocity) for chloramphenicol (~15.0 μmolar) reported by Shaw, et. al., "The Enzymatic Acetylation of Chloramphenicol by Extracts of R Factor-Resistant *Escherichia coli,*" *J. Biol. Chem.* 242(4):687 (1967). Most of the subject compounds are active as substrates for CAT, some exhibiting velocities greater than 60% of chloramphenicol. The fluorescent mono- and di-acyl derivatives of the subject compounds are easily separable from the non-acylated substrates by TLC and HPLC, allowing precise quantitation of their concentration in the assay mixture by fluorescence spectroscopy.

An example of an application of this invention is the assay of AIDS virus and human immunodeficiency virus (HIV-1) [Felber, et. al, "A Quantitive Bioassay for HIV-1 Based on Trans-Activation," *Science* 239:184 (1988)]or other viruses.

It is therefore the object of this invention to provide fluorescent derivatives of chloramphenicol for use in the detection and quantitation of enzymes which utilize chloramphenicol or its analogues as substrate. These enzymes include, but are not limited to chloramphenicol acetyltransferase (CAT).

DETAILED DESCRIPTION

Figure 1:
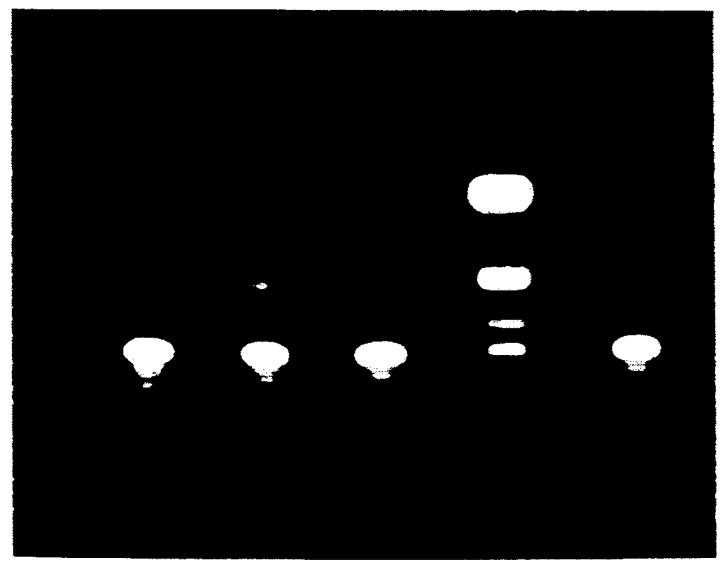
FIG. 1 is a photograph of a plate identifying CAT in cellular extracts.

The subject invention concerns reagents for use in the fluorometric determination of chloramphenicol acetyltransferase activity and methods for their use. Specifically, the reagents are fluorescent derivatives of chloramphenicol which are synthesized by reaction of D(-)threo-2-amino-1-(p-nitrophenyl)-1,3-propanediol (chloramphenicol base) or other suitable derivatives of chloramphenicol base with a suitably activated fluorescent molecule.

The chloramphenicol base derivative will normally contain a nitrogen attached to the aromatic ring at the paraposition; however other types of substituents at various locations on the aromatic ring, such as alkyl-, hydroxy-, alkoxy-, aryl-, or halo-will also be suitable for the intended use. The fluorescent moiety will normally be separated from the amine of the chloramphenicol base derivative by a chain of at least two and not more than twelve atoms other than hydrogen, the preferred number of atoms depending on the nature of the aryl substituent on the chloramphenicol base derivative. For example, a nitro- or amino- aryl substituent causes the fluorescence intensity of the fluorophore to be significantly reduced when the number of atoms in the linking chain is less than about six atoms. Increasing the length of the linking chain to six to seven atoms results in sufficient separation between the nitro- or amino- substituent and the fluorophore that the fluorescence intensity is not significantly reduced. The atoms in the linking chain may include, but are not necessarily limited to carbon, nitrogen, oxygen or sulfur.

When the linking chain contains a carbonyl group adjacent to the amine of the chloramphenicol base derivative, the bond will usually be an amide bond, formed by reaction of the amine with an activated carboxy derivative of the fluorescent molecule, or a urethane bond, formed by reaction of the amine with an activated carbonate derivative of the fluorescent molecule, or a urea bond, formed by reaction of the amine with an isocyanate derivative of the fluorescent molecule. When the linking chain contains thiocarbonyl adjacent to the amine of the chloramphenicol base derivative, the bond will usually be a thiourea bond, formed by reaction of the amine with an isothiocyanate derivative of the fluorescent compound. When the linking chain contains a sulfonyl adjacent to the amine of the chloramphenicol base derivative, the bond will usually be a sulfonamide bond, formed by reaction of the amine with an activated sulfonic acid derivative of the fluorescent compound. When the linking chain contains a methylene or methine group adjacent to the amine of the chloramphenicol base derivative, the bond will usually be formed by reductive amination of an aldehyde derivative of the fluorescent molecule or by nucleophilic displacement of a labile substituent such as halogen. These activated derivatives can be prepared in a variety of ways, which are known to persons skilled in chemistry, from carboxylic acid, hydroxyl, amine or sulfonic acid groups on the fluorescent molecule.

Unique fluorescent derivatives of chloramphenicol, according to this invention, have the general structure of formula (1):

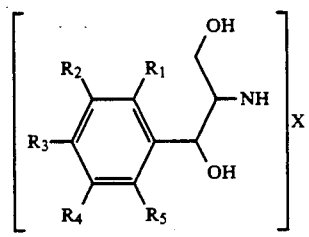

wherein:
$R_1$–$R_5$, which may be the same or different, are alkyl-, hydroxy-, alkoxy-, aryl-, halo-, nitro-, amino-, alkylamido-, or arylamido; and X is a fluorophore derived from fluorescein, rhodamine, coumarin, dimethylaminonaphthalene sulfonic acid (dansyl), pyrene, anthracene, nitrobenzoxadiazole (NBD), acridone or dipyrromethenboron difluoride.

Particularly useful compounds are those of formula (2):

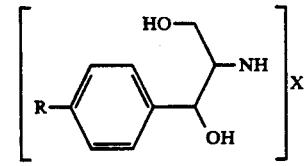

wherein:
R is an alkyl-, hydroxy-, alkoxy,- aryl-, or halo- group; or

R is a nitrogen derivative which includes nitro-, amino-, alkylamido- and arylamido-, where the aryl group is a phenyl or alkyl-substituted phenyl group.

X is a fluorescent derivative which has been attached to the nitrogen atom through a suitable covalent bond, wherein the covalent bond between the amine of the chloramphenicol base derivative and the fluorescent derivative is amide, urethane, urea, thiourea, sulfonamide or alkyl.

X is a fluorescent derivative which is separated from the amine of the chloramphenicol base derivative by a linking chain of from 1 to 12 atoms other than hydrogen, wherein the atoms in the chain are carbon, nitrogen, oxygen or sulfur.

X may be selected from, but is not necessarily limited to, the group which includes derivatives of fluorescein, rhodamine, coumarin, dimethylaminonaphthalene sulfonic acid (dansyl), pyrene, anthracene, nitrobenzoxadiazole (NBD), acridine and dipyrromethenboron difluoride.

Preferred R groups include alkylamido- (RCONH—), wherein the alkyl chain consists of from one to three carbon atoms.

Preferred linking chains between the fluorophore and the aliphatic nitrogen atom of the chloramphenicol base consist of two to four atoms other than hydrogen if R is alkylamido-, and six to twelve atoms other than hydrogen if R is nitro- or amino-.

Preferred X groups include derivatives of dipyrrometheneboron difluoride and derivatives of coumarin.

The choice of fluorophore will vary depending on compatibility with the CAT enzyme, extinction coefficient, quantum yield, desired wavelength of measurement, solubility in both aqueous and non-aqueous environments, and ease of separation of the acylation products from starting material. In order to achieve the highest sensitivity, a primary requirement is to preserve the highest possible substrate activity (compared to chloramphenicol). Other factors which contribute to high sensitivity are a high extinction coefficient and high quantum yield. Good solubility of the substrate in the enzymatic assay solution is desirable so that the concentration can be maintained at or above the $K_m$ of the enzyme (typically around 10 micromolar), while at the same time, good solubility of the acylation products in non-aqueous environment facilitates extraction of the acylation products prior to separation and extraction of the separated products from the separation medium (usually silica-gel TLC plates, as described above and in Example 48). Examples of fluorescent chloramphenicol derivatives which are the subject of this invention are given in Tables I to VIII.

TABLE I

FLUORESCENT CHLORAMPHENICOL ACETYLTRANSFERASE SUBSTRATES
Chloramphenicol-dipyrrometheneboron difluoride Derivatives

| Compound | R | X |
|---|---|---|
| 1 | Acetamido- | 1-(4,4'-Difluoro-3,5,7-trimethyl-4-bora-3a,4a-diaza-s-indaceneacetyl)-(1F) |
| 2 | Amino- | 1F |
| 3 | Nitro- | 1F |
| 4 | Nitro- | 4-((1-(4,4'-Difluoro-3,5,7-trimethyl-4-bora-3a,4a-diaza-s-indaceneacetyl)amino)butyryl)-(2F) |
| 5 | Amino- | 2F |
| 6 | Acetamido- | 2F |
| 7 | 3-Carboxypropionylamino- | 2F |
| 8 | Acetamido- | 2-(4,4'-Difluoro-1,3,5,7-tetramethyl-4-bora-3a,4a-diaza-s-indacenepropionyl)-(3F) |
| 9 | Amino- | 3F |
| 10 | Nitro- | 3F |
| 11 | Nitro- | 4-((2-(4,4'-Difluoro-1,3,5,7-tetramethyl-4-bora-3a,4a-diaza-s-indacene propionyl)amino)butyryl)-(4F) |

TABLE I-continued

FLUORESCENT CHLORAMPHENICOL ACETYLTRANSFERASE SUBSTRATES
Chloramphenicol-dipyrrometheneboron difluoride Derivatives

| Compound | R | X |
|---|---|---|
| 12 | Acetamido- | 3-(4,4'-Difluoro-5,7-dimethyl-4-bora-3a,4a-diaza-s-indacenepropionyl)-(5F) |
| 13 | Amino- | 5F |
| 14 | Nitro- | 5F |
| 15 | Acetamido- | 4-((3-(4,4'-Difluoro-5,7-dimethyl-4-bora-3a,4a-diaza-s-indacenepropionyl)amino)butyryl)-(6F) |
| 16 | 3-Carboxypropionylamino- | 6F |
| 17 | Nitro- | 6F |

TABLE II

FLUORESCENT CHLORAMPHENICOL ACETYLTRANSFERASE SUBSTRATES
Chloramphenicol-coumarin Derivatives

| Compound | R | X |
|---|---|---|
| 18 | Acetamido- | 4-(7-dimethylaminocoumarinacetyl)-(7F) |
| 19 | Amino- | 7F |
| 20 | Nitro- | 7F |
| 21 | Nitro- | 4-((4-(7-dimethyaminocoumarinacetyl)amino)butyryl)-(8F) |
| 22 | Amino- | 8 |
| 23 | Acetamido- | 8F |
| 24 | 3-Carboxypropionylamino- | 8F |
| 25 | Acetamido- | 4-((3-(4-methyl-7-hydroxycoumarinacetyl)amino)butyryl)-(9F) |
| 26 | Amino- | 9F |
| 27 | Nitro- | 9F |

TABLE III

FLUORESCENT CHLORAMPHENICOL ACETYLTRANSFERASE SUBSTRATES
Chloramphenicol-NBD Derivatives

| Compound | R | X |
|---|---|---|
| 28 | Acetamido- | 6-((4-(7-nitrobenz-2-oxa-1,3-diazolyl)amino)hexanoyl)-(10F) |
| 29 | Amino- | 10F |

TABLE IV

FLUORESCENT CHLORAMPHENICOL ACETYLTRANSFERASE SUBSTRATES
Chloramphenicol-pyrene Derivatives

| Compound | R | X |
|---|---|---|
| 30 | Acetamido- | 1-pyrenebutyryl-(11F) |

TABLE V

FLUORESCENT CHLORAMPHENICOL ACETYLTRANSFERASE SUBSTRATES
Chloramphenicol-anthracene Derivatives

| Compound | R | X |
|---|---|---|
| 31 | Acetamido- | 9-anthracenepropionyl-(12F) |

TABLE VI

FLUORESCENT CHLORAMPHENICOL ACETYLTRANSFERASE SUBSTRATES
Chloramphenicol-acridone Derivatives

| Compound | R | X |
|---|---|---|
| 32 | Acetamido- | 10-acridoneacetyl-(13F) |

TABLE VI-continued

FLUORESCENT CHLORAMPHENICOL
ACETYLTRANSFERASE SUBSTRATES
Chloramphenicol-acridone Derivatives

| Compound | R | X |
|---|---|---|
| 33 | Amino- | 13F |

TABLE VII

FLUORESCENT CHLORAMPHENICOL
ACETYLTRANSFERASE SUBSTRATES
Chloramphenicol-dansyl Derivatives

| Compound | R | X |
|---|---|---|
| 34 | Acetamido- | 4-((1-(5-dimethylaminonaphthalene sulfonyl)amino)butyryl)-(14F) |

TABLE VIII

FLUORESCENT CHLORAMPHENICOL
ACETYLTRANSFERASE SUBSTRATES
Chloramphenicol-xanthene Derivatives

| Compound | R | X |
|---|---|---|
| 35 | Acetamido- | 4-(5-(tetramethylrhodaminethioureidyl)butyryl)-(15F) |
| 36 | Acetamido- | 4-(6-(fluoresceinthioureidyl)butyryl)-(16F) |

Coumarins and dipyrromethenebioron difluoride fluorophores covalently bonded to chloramphenicol base or suitable derivatives of chloramphenicol base are particularly suitable as CAT substrates because they show superior activity as substrates, have generally high extinction coefficients and quantum yields and are readily soluble in both aqueous and non-aqueous solvents. By way of example, Compound 6 has fluorescence comparable to the corresponding fluorescein derivative 36, but is much more soluble in ethyl acetate, which is a preferred extraction solvent.

As previously discussed, the subject compounds are useful in quantitating chloramphenicol acetyltransferase activity in cell extracts. In order to perform these assays, there must be a method for accurately and precisely determining the quantity of substrate acetylated during a given time period. Measurement of the acetylation products of the subject compounds by their intrinsic fluorescence offers a practical alternative to the currently used radiographic and spectrophotometric procedures described above. Since fluorometry is a much more sensitive technique than absorptiometry, use of the subject compounds will result in an assay with superior sensitivity. In addition, the assay will take less time to complete than the tedious radiometric methods. Fluorescence measurements can be carried out directly on TLC plates by means of an incident-light fluorometer, on TLC extracts or on the effluent of a HPLC column. Although the measurement of fluorescence offers superior sensitivity when compared to measurement of absorption, it is recognized that the subject compounds for the most part have high extinction coefficients so that, in many applications, quantitation by measurement of their absorption will provide an assay with adequate sensitivity. Absorption measurements can be carried out on TLC extracts or on the effluent of a HPLC column.

The following illustrations describe the practice of the invention and are by way of example and not by way of limitation.

EXAMPLE 1

D(−)threo-2-amino-1-(p-aminophenyl)-1,3-propanediol (Compound A)

To a suspension of 1.0 g chloramphenicol base in 30 ml methanol was added 0.1 g 10% palladium on charcoal. The mixture was pressurized to 50 psi with hydrogen and shaken for one hour in a Parr hydrogenation apparatus at room temperature. The reaction mixture was filtered through a diatomateous earth pad and the filtrate was concentrated on a rotary evaporator to give a pale yellow solid. Recrystallization from methanol yielded 450 mg of off-white crystals. A second crop of 300 mg of crystals was obtained from the mother liquor after cooling in a refrigerator overnight. Total yield was 0.75 g Compound A, which was chromatographically homogeneous.

EXAMPLE 2

D(−)threo-2-(N-t-BOC-(4-aminobutyrylamino))-1-(p-nitrophenyl)-1,3-propanediol (Compound B)

To a mixture of 0.5 g chloramphenicol base, 0.48 g N-t-BOC-3-aminobutyric acid, 0.32 g hydroxybenzotriazole and 420 μL diisopropylethylamine in 20 mL THF was added 0.49 g N,N-dicyclohexyl carbodiimide. The reaction mixture was stirred at room temperature for 18 hours. The solution was filtered from precipitated dicyclohexylurea and the filtrate was evaporated on a rotary evaporator to give a yellow oil. The crude product was purified on a 2×35 cm silica gel column, eluting first with 2% methanol in chloroform, then with 5% methanol in chloroform. Evaporation of the major fraction yielded 0.75 g Compound B, isolated as a white gum-like solid which was homogeneous by TLC.

EXAMPLE 3

D(−)threo-2-(4-aminobutyrylamino)-1-(p-nitrophenyl)-1,3-propane-diol (Compound C)

Trifluoroacetic acid (10 mL) was added to 3.5 g Compound B, and the mixture was stirred at room temperature for 20 minutes. The solution was then poured into 100 mL ether with vigorous stirring and the precipitate was collected by filtration and washed several times with ether. The hygroscopic product was dried overnight in a vacuum desiccator to yield 3.1 g Compound C, which was chromatographically homogeneous.

EXAMPLE 4

D(−)threo-2-(N-t-BOC-(4-aminobutyrylamino))-1-(p-aminophenyl)-1,3-propanediol (Compound D)

To 3.0 g Compound B in 100 mL methanol was added 300 mg 10% palladium on charcoal. Hydrogenation was carried out as described in Example 1 for 30 minutes to yield 2.6 g Compound D.

EXAMPLE 5

D(—)threo-2-(N-t-BOC-(4-aminobutyrylamino))-1-(p-acetamidophenyl)-1,3-propanediol (Compound E)

To a solution of 1.5 g Compound D in 40 mL dry THF was added 400 μL acetic anhydride and the mixture was stirred at room temperature for 3 hours. The resulting reaction mixture was concentrated on a rotary evaporator and the residual oil was purified by silica gel column chromatography (2×25 cm column), eluting with 10% methanol in chloroform. After removal of the solvent from the major fraction, a yield of 1.4 g of the desired product, Compound E, was obtained.

EXAMPLE 6

D(—)threo-2-(4-aminobutyrylamino)-1-(p-acetamidophenyl)-1,3-propanediol (Compound F)

To 1.4 g Compound E was added 5 mL trifluoroacetic acid. After stirring at room temperature for 30 minutes, the reaction mixture was worked up as described in Example 3 to yield 0.9 g Compound F.

EXAMPLE 7

D(—)threo-2-(N-t-BOC-(4-aminobutyrylamino))-1-(p-(3-carboxypropionylaminophenyl))-1,3-propanediol (Compound G)

To a solution of 0.5 g Compound D was added 0.14 g succinic anhydride. The solution was stirred at room temperature for 8 hours and concentrated on a rotary evaporator to yield a crude oil. This crude product was subjected to silica gel column chromatography (2×15 cm column), eluting with 20% methanol in chloroform. The yield of the product, Compound G, was 0.32 g.

EXAMPLE 8

D(—)threo-2-(4-aminobutyrylamino)-1-(p-(3-carboxypropionylaminophenyl))-1,3-propanediol (Compound H)

Trifluoroacetic acid (10 mL) was added to 0.32 g Compound G. The mixture was stirred 30 minutes at room temperature and worked up as described in Example 3 to yield 190 mg Compound H.

EXAMPLE 9

D(—)threo-2-(4-aminobutyrylamino)-1-(p-aminophenyl)-1,3-propanediol (Compound I)

To a sample of 0.69 q Compound D was added 3 mL trifluoroacetic acid. After stirring at room temperature for 30 minutes, the reaction mixture was worked up as described in example 3 to yield to yield 0.45 g Compound I.

EXAMPLE 10

N-2-(D(—)threo-1-(p aminophenyl)-1,3-dihydroxypropyl)-4,4'-difluoro-3,5,7-trimethyl-4-bora-3a,4a-diaza-s-indacene-1-acetamide (Compound 2)

To a suspension of 10 mg Compound A in 5 mL dry DMF was added 25 μL triethylamine. After stirring at room temperature for a few minutes, 21 mg of the succinimidyl ester of Compound 1F was added. The mixture was stirred overnight at room temperature. The solution was concentrated on a rotary evaporator and the residue was purified by silica-gel chromatography (1×20 cm column), eluting with 5% methanol in chloroform. The major fractions were combined and evaporated to yield 14 mg Compound 2.

EXAMPLE 11

N-2-(D(—)threo-1-(p-acetamidophenyl)-1,3-dihydroxypropyl)-4,4'-difluoro-3,5,7-trimethyl-4-bora-3a,4a-diaza-s-indacene-1-acetamide (Compound 1)

Compound 2 (8 mg) was dissolved in 2 mL acetone and 5 drops acetic anhydride was added. The solution was stirred at room temperature for 1 hour, then concentrated on a rotary evaporator. The crude product was purified by silica-gel chromatography (1×15 cm column) as in Example 10, to yield 8 mg Compound 1.

EXAMPLE 12

N-2-(D(—)threo-1-(p-aminophenyl)-1,3-dihydroxypropyl)-4,4'-difluoro-1,3,5,7-tetramethyl-4-bora-3a,4a-diaza-s-indacene-2-propionamide (Compound 9)

To a suspension of 10 mg Compound A in 5 mL dry DMF was added 25 μL triethylamine. After stirring at room temperature for a few minutes, the succinimidyl ester of Compound 3F was added and the solution was stirred at room temperature overnight. The reaction mixture was worked up as described in Example 10 giving 20 mg Compound 9.

EXAMPLE 13

N-2-(D(—)threo-1-(p-acetamidophenyl)-1,3-dihydroxypropyl)-4,4'-difluoro-1,3,5,7-tetramethyl-4-bora-3a,4a-diaza-s-indacene-2-propionamide (Compound 8)

10 mg Compound 9 in 2 mL acetone was added 5 drops acetic anhydride and the mixture was stirred for 1 hour at room temperature. The solvent was removed on a rotary evaporator and the residual solid was dissolved in a minimum amount of DMF and chromatographed on a 1×20 cm silica-gel column, eluting with 8% methanol in chloroform. The major fraction was combined and the solvent evaporated to yield 10 mg Compound 8.

EXAMPLE 14

N-2-(D(—)threo-1-(p-aminophenyl)-1,3-dihydroxypropyl)-4,4'-difluoro-5,7-dimethyl-4-bora-3a,4a-diaza-s-indacene-3-propionamide (Compound 13)

Triethylamine (25 μL) was added to a suspension of 10 mg Compound A in 2 mL dry THF and the mixture was stirred for a few minutes. Then 21 mg of the succinimidyl ester of Compound 5F was added and the solution was stirred at room temperature overnight. Work-up of the crude reaction mixture was performed as described in Example 10, using a 1×10 cm silica-gel column, to yield 20 mg Compound 13.

EXAMPLE 15

N-2-(D(—)threo-1-(p-acetamidophenyl)-1,3-dihydroxypropyl)-4,4'-difluoro-5,7-dimethyl-4-bora-3a,4a-diaza-s-indacene-3-propionamide (Compound 12)

Two drops acetic anhydride was added to a solution of 15 mg Compound 13 in 0.5 mL acetone and the mixture was stirred at room temperature for 1 hour. After addition of 1 mL of methanol to quench the reaction, the solvent was removed on a rotary evaporator and the residue was purified on a 2×10 cm silica-gel column, eluting with 5% methanol in chloroform to yield 12 mg of Compound 12.

EXAMPLE 16

4-(N-2-(D(—)threo-1-(p-acetamidophenyl)-1,3-dihydroxypropyl)-(3-(4,4'-difluoro-5,7-dimethyl-4-bora-3a,4a-diaza-s-indacenepropionyl)amino)butyramide (Compound 15)

To a solution of 17 mg Compound F in 0.2 mL dry DMF was added 10 µL of triethylamine. Then 15 mg of the succinimidyl ester of Compound 5F in 1 mL dry DMF was added and the mixture was stirred at room temperature overnight. Work-up of the crude reaction mixture, as described in Example 10, using a 1.5 cm×5 cm silica-gel column gave 13 mg of Compound 15.

EXAMPLE 17

4-(N2-(D(—)threo-1-(p-aminophenyl)-1,3-dihydroxypropyl)-(1-(4,4'-difluoro-3,5,7-trimethyl-4-bora-3a,4a-diaza-s-indaceneacetyl)amino)butyramide (Compound 5)

To a solution of 16 mg of Compound I in 0.5 mL dry DMF was added 2.0 mL Dry THF. Then 10 µL of triethylamine was added, followed by 15 mg of the succinimidyl ester of Compound 1F. The reaction mixture was stirred at room temperature overnight. Work-up of the crude reaction mixture was accomplished as described in Example 10, using a 1.5×20 cm silica-gel column, eluting with 8% methanol in chloroform, gave 11 mg of Compound 5.

EXAMPLE 18

4-(N-2-(D(—)threo-1-(p-(3-carboxypropionylaminophenyl))-1,3-dihydroxypropyl)-(1-(4,4'-difluoro-3,5,7-trimethyl-4-bora-3a,4a-diaza-s-indaceneacetyl)amino)butyramide (Compound 7)

To a suspension of 6.0 mg of Compound 5 in 5 mL of chloroform was added 1.1 mg of succinic anhydride. The mixture was stirred overnight. A precipitate formed, which was filtered and washed thoroughly with chloroform TLC showed the presence of a single product. The precipitate was dried under vacuum at room temperature to yield 5 mg of Compound 7.

EXAMPLE 19

4-(N-2-(D(—)threo-1-(p-acetamidophenyl)-1,3-dihydroxypropyl)-(1-(4,4'-difluoro-3,5,7-trimethyl-4-bora-3a,4a-diaza-s-indaceneacetyl)amino)butyramide (Compound 6)

To a solution of 17 mg of Compound F in 0.5 mL of dry DMF was added 3 mL of dry THF. Then, 10 µL of triethylamine was added, followed by 15 mg of Compound IF. The mixture was stirred overnight at room temperature. The crude reaction mixture was chromatographed on a 1×20 cm silica-gel column as described in Example 10, using 8% methanol in chloroform to yield 14 mg of Compound 6.

EXAMPLE 20

4-(N-2-(D(—)threo-1-(p-(3-carboxypropionylaminophenyl))-1,3-dihydroxypropyl)-(3-(4,4'-difluoro-5,7-dimethyl-4-bora-3a,4a-diaza-s-indacenepropionyl)amino)butyramide (Compound 16)

To a solution of 13 mg Compound H in 1 mL dry DMF was added 10 µL of triethylamine and 10 mg of the succinimidyl ester of Compound 5F. The reaction mixture was stirred at room temperature overnight and the product isolated by silica-gel chromatography as described in Example 10, using 10% methanol in methylene chloride. The yield of Compound 16 was 14 mg.

EXAMPLE 21

N-2-(D(—)threo-1-(p-nitrophenyl)-1,3-dihydroxypropyl)-3-(4,4'-difluoro-5,7-dimethyl-4-bora-3a,4a-diaza-s-indacenepropionamide (Compound 17)

To a solution of 10 mg of chloramphenicol base in 1 mL of dry THF was added 10 µL of triethylamine, followed by 18 mg of the succinimidyl ester of Compound 5F. The reaction mixture was stirred at room temperature overnight. The reaction mixture was concentrated and the residue was purified by column chromatography (1.5×10 cm silica-gel), first eluting with 2% methanol in methylene chloride until the minor impurities were removed, then with 7% methanol in methylene chloride. The yield of Compound 17 was 19 mg.

EXAMPLE 22

N-2-(D(—)threo-1-(p-nitrophenyl)-1,3-dihydroxypropyl)-1-(4,4'-difluoro-3,5,7-trimethyl-4-bora-3a,4a-diaza-s-indaceneacetamide (Compound 3)

To a solution of 14 mg of chloramphenicol base and 10 µL of triethylamine in 1 mL of dry THF was added 25 mg of the succinimidyl ester of Compound 1F and the mixture was stirred at room temperature overnight. The solvent was removed on a rotary evaporator and the residual oil was purified by preparative TLC on 20×20 cm x 250 micron silica-gel plates. The plates were eluted 3 times with 3% methanol in chloroform, and the major band was extracted with chloroform. After evaporation of the solvent, TLC showed a small amount of impurity. The oil was dissolved in 10 mL of chloroform and extracted with 5% sodium bicarbonate solution. The chloroform layer was dried over sodium sulfate and evaporated under vacuum to yield 22 mg of Compound 3.

EXAMPLE 23

4-(N-2-(D(—)threo-1-(p-nitrophenyl)-1,3-dihydroxypropyl)-(1-(4,4'-difluoro-3,5,7-trimethyl-4-bora-3a,4a-diaza-s-indaceneacetyl)amino)butyramide (Compound 4)

To a solution of 11 mg of Compound C in 0.5 mL of dry DMF was added 25 μL of triethylamine followed by 10 mg of the succinimidyl ester of Compound IF. The reaction mixture was stirred at room temperature overnight and the solvent was removed under vacuum to yield a red-orange solid. The crude product was purified as described in Example 10 to yield 11 mg of Compound 4.

EXAMPLE 24

N-2-(D(—)threo-1-(p-nitrophenyl)-1,3-dihydroxypropyl)-2-(4,4'-difluoro-1,3,5,7-tetramethyl-4-bora-3a,4a-diaza-s-indacenepropionamide)

(Compound 10)

To a suspension of 10 mg of chloramphenicol base in 3 mL of dry THF was added 10 μL of triethylamine. The suspension was stirred several minutes whereupon all the solid material was completely dissolved. Then 15 mg of the succinimidyl ester of Compound 3F was added and the resulting mixture was stirred at room temperature for two days. The crude reaction mixture was concentrated under vacuum and the oily residue was purified by preparative TLC on silica-gel plates as described in Example 22 to yield 18 mg of Compound 10.

EXAMPLE 25

4-(N-2-(D(—)threo-1-(p-nitrophenyl)-1,3-dihydroxypropyl)-(2-(4,4'-difluoro-1,3,5,7-tetramethyl-4-bora-3a,4a-diaza-s-indacenepropionyl)amino)butyramide (Compound 11)

To a solution of 10 mg of Compound C in 0.5 mL of dry THF was added 25 μL of triethylamine followed by 10 mg of the succinimidyl ester of Compound 3F and the mixture was stirred at room temperature for four days. The solvent was evaporated and the crude product was chromatographed on a 1×20 cm silica-gel column, eluting with chloroform to yield 12 mg of Compound 11.

EXAMPLE 26

4-(N-2-(D(—)threo-1-(p-nitrophenyl)-1,3-dihydroxypropyl)-(3-(4,4'-difluoro-5,7-dimethyl-4-bora-3a,4a-diaza-s-indacenepropionyl)amino)butyramide (Compound 14)

To a suspension of 20 mg of Compound C in 3 mL of dry THF was added 10 μL of triethylamine, followed by the addition of 19 mg of the succinimidyl ester of compound 5F. The reaction mixture was stirred overnight at room temperature and the solvent was removed under vacuum. The crude product was purified by column chromatography (1.5×10 cm) on silica-gel as described in example 21 to yield 18 mg Compound 14.

EXAMPLE 27

N-2-(D(—)threo-1-(p-aminophenyl)-1,3-dihydroxypropyl)-7-dimethylaminocoumarin-4-acetamide (Compound 19)

To a suspension of 25 mg of the succinimidyl ester of Compound 7F in 5 mL of dry THF was added one drop of triethylamine and 14 mg of Compound A. The reaction mixture was stirred at room temperature overnight, filtered and the solvent removed under vacuum. The resulting crude product was purified by silica-gel column chromatography (1×20 cm), eluting with 5% methanol in chloroform. A yield of 23 mg of Compound 19 was obtained.

EXAMPLE 28

N-2-(D(—)threo-1-(p-acetamidophenyl)-1,3-dihydroxypropyl)-7-dimethylaminocoumarin-4-acetamide (Compound 18)

To a suspension of Compound 19 in 2 mL of acetone was added five drops of acetic anhydride and the mixture was stirred at room temperature for 2 hours. The reaction mixture was still heterogeneous, so 0.5 mL of dry DMF and an additional 3 drops of acetic anhydride was added. After a total of 3 hours reaction time, the crude reaction mixture was reduced under vacuum and the residual DMF solution was poured into 30 mL of ether. The pale yellow solid was collected by filtration and the crude product was purified by silica-gel column chromatography (1×15 cm). The crude product was dissolved in a minimum amount of DMF and then loaded on the column and eluted with 5% methanol in chloroform. In this manner, 9 mg of Compound 18 was obtained.

EXAMPLE 29

N-2-(D(—)threo-1-(p-nitrophenyl)-1,3-dihydroxypropyl)-7-dimethylaminocoumarin-4-acetamide (Compound 20)

To a solution of 20 mg of the succinimidyl ester of compound 7F in 2 mL of dry THF was added 20 μL of triethylamine and 13 mg of chloramphenicol base. The reaction mixture was stirred at room temperature for 6 hours and the precipitate was filtered. The product, Compound 20 was homogeneous by TLC and therefore needed no further purification.

EXAMPLE 30

4-(N-2-(D(—)threo-1-(p-nitrophenyl)-1,3-dihydroxypropyl)-(4-(7-dimethylaminocoumarinacetyl)amino)-butyramide (Compound 21)

To a solution of 24 mg of Compound C in 1 mL of dry THF was added 3 drops of triethylamine, followed by the addition of 20 mg of the succinimidyl ester of Compound 7A. The reaction mixture was stirred at room temperature overnight. The resulting precipitate was filtered off and purified by column chromatography on silica-gel (2×15 cm), eluting with 5% ethanol in chloroform. A yield of 7 mg of Compound 21 was obtained.

EXAMPLE 31

4-(N-2-(D(—)threo-1-(p-aminophenyl)-1,3-dihydroxy-propyl)-(4-(7-dimethylaminocoumarinacetyl)amino)-butyramide (Compound 22)

A sample of 29 mg of Compound I was dissolved in 0.5 mL of dry DMF. To this solution was added 15 μL of triethylamine and 25 mg of the succinimidyl ester of Compound 7F and the reaction mixture was stirred overnight. The solvent was removed under vacuum and the residue was purified by column chromatography on silica-gel (2×15 cm), eluting with 10% methanol in chloroform. Three fractions were obtained. The first fraction contained mainly a single product, the second and third fractions contained the product of the first fraction and a second product which had a lower Rf value (silica-gel TLC). The second and third fractions were combined and chromatographed again under the same conditions. A yield of 0.2 mg of Compound 22 was obtained.

EXAMPLE 32

4-(N-2-(D(—)threo-1-(p-acetamidophenyl)-1,3-dihydroxypropyl]-(4-(7-dimethylaminocoumarinacetyl-)amino)butyramide (Compound 23)

To a solution of 65 mg of Compound F in 12 mL of 10% DMF in THF was added 30 μL of triethylamine and 50 mg of the succinimidyl ester of Compound 7F. The reaction mixture was stirred at room temperature overnight. The resulting precipitate was filtered and the solid was washed several times with dry THF. After drying, 70 mg of Compound 23 was obtained.

EXAMPLE 33

4-(N-2-(D(—)threo-1-(p-(3-carboxypropionylaminophenyl))-1,3-dihydroxypropyl)-(4-(7-dimethylaminocoumarinacetyl)amino)butyramide (Compound 24)

A sample of 42 mg of Compound H was dissolved in 3 mL of dry 1:3 DMF in THF. Into the above solution was added 20 μL of triethylamine followed by 30 mg of the succinimidyl ester of 7F.

The reaction mixture was stirred at room temperature overnight, concentrated under vacuum and the residue purified by silica-gel column chromatography (2×10 cm column). elution was carried out with 0.2% acetic acid, 20% methanol in chloroform. A yield of 17 mg of Compound 24 was obtained.

EXAMPLE 34

4-(N-2-(D(—)threo-1-(p-acetamidophenyl)-1,3-dihydroxypropyl)-(3-(4-methyl-7-hydroxycoumarinacetyl-)amino)butyramide (Compound 25)

To a solution of 13 mg of Compound F in 3 mL of 1:3 dry DMF in THF was added 10 μL of triethylamine and 10 mg of the succinimidyl ester of 4-methylcoumarin-3-acetic acid. The reaction mixture was stirred at room temperature overnight, concentrated under vacuum and the residue was purified by silica-gel column chromatography (2×10 cm column), eluting with 5% methanol in chloroform. The yield of Compound 25 was 9 mg.

EXAMPLE 35

4-(N-2-(D(—)threo-1-(p-nitrophenyl)-1,3-dihydroxypropyl)-(3-(4-methyl-7-hydroxycoumarinacetyl-)amino)butyramide (Compound 26)

To a solution of 13 mg of Compound C in 2 mL of dry DMF was added 10 μL of triethylamine, followed by the addition of 10 mg of the succinimidyl ester of 4-methylcoumarin-3-acetic acid. The reaction mixture was stirred at room temperature overnight, concentrated under vacuum and the residue was purified as described in Example 34. The yield of Compound 25 was 11 mg.

EXAMPLE 36

4-(N-2-(D(—)threo-1-(p-aminophenyl)-1,3-dihydroxypropyl)-(3-(4-methyl-7-hydroxycoumarinacetyl-)amino)butyramide (Compound 27)

To a solution of 5 mg of Compound 26 in 2 mL of methanol in a test tube was added a magnetic stir bar and a few mg palladium on charcoal. Hydrogen gas was bubbled through the solution while stirring vigorously for 10 minutes. The reaction mixture was filtered through a diatomaceous earth pad, the solvent was evaporated and the residual solid was purified by column chromatography (2×10 cm silica-gel column), eluting with 10% methanol in chloroform. The yield of Compound 27 was 2 mg.

EXAMPLE 37

6-(N-2-(D(—)threo-1-(p-aminophenyl)-1,3-dihydroxypropyl)-(4-(7-nitrobenz-2-oxa-1,3-diazolyl)amino)hexanamide (Compound 28)

To a solution of 7 mg of Compound A in 2 mL of dry THF was added 10 μL of triethylamine, followed by the addition of 16 mg of The succinimidyl ester of Compound 10F. The reaction mixture was stirred overnight at room temperature. The solvent was removed under vacuum and the residue was purified by silica-gel column chromatography (1×10 cm column), eluting with 5% methanol in methylene chloride, to yield 18 mg of Compound 28.

EXAMPLE 38

6-(N-2-(D(—)threo-1-(p-aminophenyl)-1,3-dihydroxypropyl)-(4-(7-nitrobenz-2-oxa-1,3-diazolyl)amino)hexanamide (Compound 29)

To a solution of 12 mg of Compound 28 in 1 mL of dry THF was added one drop of acetic anhydride and the mixture was stirred at room temperature for 1 hour. The 5 mL of methanol was added and the mixture was stirred for a few minutes. The solvent was removed under vacuum and the residue was purified by silica-gel column chromatography (1.5×15 cm column), eluting with 5% methanol in dichloromethane, to yield 10 mg of Compound 29.

EXAMPLE 39

N-2-(D(—)threo-1-(p-aminophenyl)-1,3-dihydroxypropyl)-1-pyrenebutyramide (Compound J)

To a solution of 10 mg of Compound A in 2 mL of dry THF was added 15 μL of triethylamine, followed by the addition of 21 mg of succinimidyl pyrene-1-butyrate. The reaction mixture was stirred at room temperature overnight, reduced to dryness under vacuum and the residue subjected to purification by silica-gel column chromatography (1.5×15 cm column), eluting with 3% methanol in methylene chloride. The yield of Compound J was 22 mg.

EXAMPLE 40

N-2-(D(—)threo-1-(p-acetamidophenyl)-1,3-dihydroxypropyl)-1-pyrenebutyramide (Compound 30)

To a solution of 20 mg of Compound J in 1 mL of dry THF was added one drop of acetic anhydride and the mixture was stirred at room temperature for 1 hour. Then 0.5 mL of methanol was added and stirring was continued for several minutes. The solvent was removed under vacuum and the residue was subjected to column chromatography on silica-gel (1.5×15 cm column), eluting with 5% methanol in chloroform to yield 15 mg of Compound 30.

EXAMPLE 41

N-2-(D(—)threo-1-(p-aminophenyl)-1,3-dihydroxypropyl)-9-anthracenepropionamide (Compound K)

To a solution of 10 mg of Compound A in 2 mL of dry DMF was added 15 μL of triethylamine, followed by the addition of 20 mg of succinimidyl anthracene-9-propionate, and the mixture was stirred at room temperature overnight. The solvent was removed under vacuum and the residue purified on a 1.5×15 cm silica-gel column, eluting with 3% methanol in chloroform to give 19 mg of Compound K, contaminated with an impurity, probably anthracene-9-propionic acid.

EXAMPLE 42

N-2-(D(—)threo-1-(p-acetamidophenyl)-1,3-dihydroxypropyl)-9-anthracenepropionamide (Compound 31)

To a solution of 15 mg of Compound K in 1 mL of dry THF was added one drop of acetic anhydride and the reaction mixture was stirred at room temperature for 1 hour. Then 0.5 mL of methanol was added and stirring was continued for several minutes. The solvent was removed under vacuum and the residue was purified on a 1.5×15 cm silica-gel column, eluting with 5% methanol in methylene chloride, to give 7 mg of Compound 31.

EXAMPLE 43

N-2-(D(—)threo-1-(p-aminophenyl)-1,3-dihydroxypropyl)-10-acridoneacetamide (Compound 33)

To a solution of 10 mg of Compound A in 2 mL of dry DMF was added 15 μL of triethylamine, followed by the addition of 19 mg of succinimidyl acridone-10-acetate and the reaction mixture was stirred at room temperature overnight. The resulting white precipitate was collected by filtration and the solid was washed several times with ether to yield, after drying, 14 mg of Compound 33.

EXAMPLE 44

N-2-(D(—)threo-1-(p-acetamidophenyl)-1,3-dihydroxypropyl)-10-acridoneacetamide (Compound 32)

To a solution of 12 mg of Compound 33 in 0.5 mL of dry DMF was added one drop of acetic anhydride and the mixture was stirred at room temperature for one hour. Then 0.5 mL of methanol was added and the mixture was stirred a few more minutes. The solvent was removed under vacuum and the residue was purified on a 1.5×15 cm silica-gel column, eluting with 10% methanol in methylene chloride to yield 10 mg of Compound 32.

EXAMPLE 45

4-(N-2-(D(—)threo-1-(p-acetamidophenyl)-1,3-dihydroxypropyl)-(1-(5-dimethylaminonaphthalenesulfonyl)amino)butyramide (Compound 34)

To a solution of 10 mg of Compound F in 0.5 mL of dry DMF was added 10 μL of triethylamine, followed by 7 mg of 5-dimethylaminonaphthalenesulfonyl chloride. The reaction mixture was stirred at room temperature overnight and the solvent was removed under vacuum. The crude product was purified using a 1.5×15 cm silica-gel column, eluting with 10% methanol in methylene chloride. A yield of 8 mg of Compound 34.

EXAMPLE 46

4-(N-2-(D(—)threo-1-(p-acetamidophenyl)-1,3-dihydroxypropyl)-(5-(tetramethylrhodaminethioureidyl)amino)butyramide (Compound 35)

To a solution of 5 mg of Compound F in 0.5 mL of dry DMF was added 10 μL of triethylamine, followed by the addition of 5 mg of tetramethylrhodamine-5-isothiocyanate and the mixture was stirred at room temperature overnight. The solvent was removed under vacuum and the crude product was chromatographed on a 1.5×5 cm silica-gel column, eluting with 20% methanol in methylene chloride, to give 3 mg of Compound 35.

EXAMPLE 47

4-(N-2-(D(—)threo-1-(p-acetamidophenyl)-1,3-dihydroxypropyl)-(6-(fluoresceinthioureidyl)amino)butyramide (Compound 36)

To a solution of 10 mg of Compound F in 0.5 mL of dry DMF was added 10 μL of triethylamine, followed by 10 mg of fluorescein-6-isothiocyanate. The reaction mixture was stirred at room temperature overnight and then concentrated under vacuum. The residue was subjected to silica-gel chromatography (1.5×10 cm column), eluting with 15% methanol in dichloromethane, to give 11 mg of Compound 36.

EXAMPLE 48

Procedure for Comparing Activity of Fluorescent Substrates

To a solution of 0.5 mg acetyl CoA in 112 µL of 1M TRIS pH 7.4 was added 7 µL of a solution of 440 uM fluorescent CAT substrate in ethanol. Then 0.8 U of purified CAT in 1 µL of 1M TRIS (pH 7.4) was added and the solution was incubated at 37° C. for 1 hour. The reaction mixture was extracted with 0.7 mL of ethyl acetate, and the solvent was removed under vacuum. The residue was dissolved in 14 µL of ethyl acetate, spotted on the pre-absorbent area of Whatman LK6 silica-gel TLC plates and developed with 10% methanol in chloroform. A control, run as above but with no enzyme present, was spotted adjacent to each reaction mixture.

Qualitative estimates of substrate activity of each fluorescent derivative were made by examination of the plates for conversion to acetylated products. Compounds 6, 21, 23 and 28 appeared to have the highest reaction velocities of the tested fluorescent substrates.

EXAMPLE 49

Determination of $K_m$ for Compound 6

The $K_m$ was determined for Compound 6 using a direct linear plot [Eisenthal, et. al., "The Direct Linear Plot. A New Graphical Proceedure for Estimating Enzyme Kinetic Parameters," *Biochem. J.* 139:715 (1974)]. Four different concentrations of substrate, 1, 8, 12 and 40 µM, were incubated with 0.8U of purified enzyme and 0.4 mg Acetyl CoA in 0.5M TRIS, pH 7.4 for 2.5 min. The initial concentrations were determined spectroscopically using the extinction coefficient of Compound 6 (76,000). The conversion from substrate to acetylation products was determined by extraction from the TLC separation and measuring fluorescence at 532 nm with excitation at 504 nm. The reaction velocity in picomoles/min was calculated from the concentration. A plot of reaction velocity vs initial concentration was made for each of the four different concentrations, assuming the velocity at 2.5 minutes did not differ significantly from initial velocity. The $K_m$, 2.0 µM, was read from the X-axis at the point where the four rate curves intersect.

EXAMPLE 50

Relative Velocity of Compound 6 vs Choramphenicol

The velocity during the first ten minutes at a substrate concentration of 33.2 µM was determined using Compound 6 and $^{14}C$ chloramphenicol. The reactions were run in 100 µL final volume TRIS pH 7.4 with 0.4 mg of Acetyl CoA and 0.8U of purified enzyme. The concentrations of acetylated products after ten minutes were determined by extraction from the TLC plates and measuring spectrophotometrically, in the case of Compound 6, and by counting radioactivity in the case of $^{14}C$ chloramphenicol. The velocity during the first ten minutes was assumed to be very close to $V_{max}$. The velocity of Compound 6 was 0.66 of the velocity of $^{14}C$ chloramphenicol.

EXAMPLE 51

Use of Compound 6 with Cellular Extracts

Cellular extracts from cultures of cerebral astrocytes from rats transfected with the plasmid pENKAT-12 (CAT gene driven by the enkephalin promoter) were prepared. To 85 µL of this extract (in 0.25M TRIS pH 7.4) was added 33 µL TRIS pH 7.4, 0.5 mg Acetyl CoA and 7µL of a 440 µM ethanol solution of Compound 6. The mixture was incubated at 37° C. for 4 hr. FIG. 1 shows the results of this experiment: lane 1 (from the left)—cells transfected, but not stimulated; lane 2—transfected cells stimulated by 500µM 8-chlorophenylthio-cAMP; lane 3—transfected cells stimulated by $10^{-6}M$ isoproterenol, a β-adrenergic stimulator; lane 4—positive control with purified CAT enzyme; lane 5—negative control with no cell extract or enzyme.

EXAMPLE 52

Use of Fluorescent Compound in Assay of HIV-1

A specific and sensitive assay for functional AIDS virus (HIV-1) was published by Felber et al. This assay is based on cell lines containing the CD4 receptor for HIV-1. The genome of these cell lines been altered to contain the CAT gene under the control of the HIV regulatory region (long terminal repeat). Since HIV-1 virus produces its own transcriptional activator, known as tat, which acts on the HIV regulatory region, presence of functional virus in the altered cell line will induce transcription of not only the virus itself, but also the CAT gene. If any material (including both cells and cell-free fluid) containing functional HIV-1 virus is introduced to a culture of the altered cell line, CAT enzyme is induced greater than 500-fold over basal levels. Therefore, one is able to detect actual HIV virus in clinical samples rather than antibodies to the virus whose production can be hindered by disease. This method could also be adapted to detect other viruses which produce specific activator proteins.

Proposed Procedure: Add the clinical sample to a dish containing the altered cell line. Culture cells for 1 to 2 days. Either make a crude cell extract or incubate the cells with the fluorescent substrate. Measure the amount of acetylation of the substrate as described in Example 51. A significant amount of acetylation would be a specific indicator of actual HIV-1 virus in the clinical sample.

The use of a fluorescent CAT substrate rather than radiolabeled chloramphenicol would not only eliminate the problems of handling of radioactive materials, but also speed the assay time (immediate detection on a TLC plate versus sixteen hour autoradiography). Furthermore, fluorescence detection may allow a much simpler adaptation of this technique to automated analysis.

It is to be understood that, while the foregoing invention has been described in detail by way of illustration and example, only the preferred or specific embodiments have been revealed, and that numerous modifications, substitutions, and alterations are all permissible without departing from the spirit or scope of the invention as described in the following claims.

We claim:

1. A compound of the formula:

BASE—N,—*X a) where BASE is:

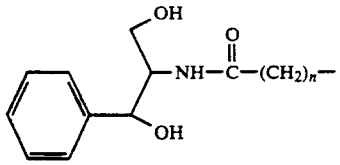

substituted at one to five aromatic ring positions by substituents, which may be the same or different, that are alkyl-, hydroxy-, alkoxy-, aryl-, halo-, nitro-, amino-, alkylamido- (where the alkyl portion contains 1-3 carbons, or arylamido- (where the aryl portion is a phenyl or alkyl-substituted phenyl) and n is greater than 0 and less than 6; and b) *X is a non-reduced tricyclic difluoroboradiazaindacene fluorophore covalently bound to the terminal $CH_2$ of BASE through a linker $N_s$; such that c) $N_s$—*X is amino-linked (—NH—*X), acetamido-linked (—NHCOCH$_2$—*X), propionamido-linked (—NHCOCH$_2$CH$_2$—*X), sulfonamido-linked (—NHSO$_2$—*X), carboxamido-linked (—NHCO—*X), ureidyl-linked (—NHCONH—*X), thioureidyl-linked (—NHCSNH—*X), or linked by a covalent bond, to said terminal $CH_2$ of BASE.

2. A compound of the formula:

a) where BASE is:

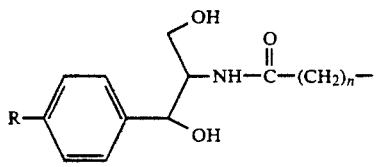

where R is alkyl-, hydroxy-, alkoxy-, aryl-, halo-, nitro-, amino-, alkylamido- (where the alkyl portion contains 1-3 carbons), or arylamido- (where the aryl portion is a phenyl or alkyl-substituted phenyl), and n is greater than 0 and less than 6;

b) *X is a non-reduced tricyclic difluoroboradiazaindacene fluorophore covalently bound to the terminal $CH_2$ of BASE through a linker $N_s$; such that c) $N_s$—*X is amino-linked (—NH—*X), acetamido-linked (—NHCOCH$_2$—*X), propionamido-linked (—NHCOCH$_2$CH$_2$—*X), sulfonamido-linked (—NHSO$_2$—*X), carboxamido-linked (—NHCO—*X), ureidyl-linked (—NHCONH—*X), thioureidyl-linked (—NHCSNH—*X), or linked by a covalent bond, to said terminal $CH_2$ of BASE.

3. A compound, as claimed in claim 1, wherein the fluorophore *X has the formula:

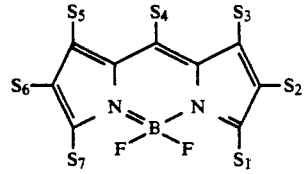

where BASE-$N_s$— is attached to said fluorophore at one of $S_1$-$S_7$, and the remainder of $S_1$-$S_7$, which may be the same or different, are hydrogen or alkyl-.

4. A compound, as claimed in claim 3, where BASE is substituted at one aromatic position by a substituent that is alkylamido-.

5. A compound, as claimed in claim 4, where n=5 and $N_s$—*X is acetamido-linked (—NHCOCH$_2$—*X) or propionamido-linked (—NHCOCH$_2$CH$_2$—*X) to said terminal $CH_2$ of BASE; or n is 1 or 2 and $N_s$ is a covalent bond.

6. A compound, as claimed in claim 2, wherein the fluorophore *X has the formula:

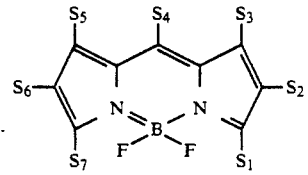

where BASE—$N_s$— is attached to said fluorophore at one of $S_1$-$S_7$, and the remainder of $S_1$-$S_7$, which may be the same or different, are hydrogen or alkyl-.

7. A compound, as claimed in claim 6, wherein R is acetamido-.

8. A compound, as claimed in claim 7, wherein n is 5 and $N_s$ is acetamido (—CH$_2$CONH—), or propionamido (—CH$_2$CH$_2$CONH—), or n is less than 3 $N_x$ is a covalent bond.

* * * * *

UNITED STATES PATENT AND TRADEMARK OFFICE
CERTIFICATE OF CORRECTION

PATENT NO. : 5,262,545
DATED : November 16, 1993
INVENTOR(S) : Haugland, et al.

It is certified that error appears in the above-indentified patent and that said Letters Patent is hereby corrected as shown below:

Item [19],
On the cover page, directly below United States Patent, "Haughland et al." should be --Haugland et al.--.

Item [75],
On the cover page, in the Inventors, "Haughland" should be --Haugland--.

At col 10, line 43 "10 mg" should be --To a solution of 10 mg--.

Signed and Sealed this

Eighth Day of October, 1996

Attest:

BRUCE LEHMAN

Attesting Officer    Commissioner of Patents and Trademarks